United States Patent [19]

Chan

[11] 4,205,168

[45] May 27, 1980

[54] N-CARBAMYLALKYL-2,6-DIALKYL-α-HALOACETANILIDES

[75] Inventor: David C. K. Chan, San Francisco, Calif.

[73] Assignee: Chevron Research Company, San Francisco, Calif.

[21] Appl. No.: 400,287

[22] Filed: Sep. 24, 1973

[51] Int. Cl.$^2$ .................. C07D 295/00; C07C 103/24
[52] U.S. Cl. ........................................ 544/165; 71/94; 71/118; 260/326.5 J; 260/558 R; 260/558 A; 546/226

[58] Field of Search ............... 260/247.2 A, 558 A, 260/558 R, 326.5 J; 544/165; 546/226

[56] References Cited

U.S. PATENT DOCUMENTS 3,780,090  12/1973  Akiba .............................. 260/471 A Primary Examiner—Paul J. Killos
Attorney, Agent, or Firm—J. A. Buchanan, Jr.; T. G. DeJonghe

[57] ABSTRACT

N-carbamylalkyl-2,6-dialkyl-α-haloacetanilides have herbicidal activity, particularly in pre-emergent applications against grassy weeds.

19 Claims, No Drawings

N-CARBAMYLALKYL-2,6-DIALKYL-α-HALOACETANILIDES

DESCRIPTION OF THE PRIOR ART

U.S. Pat. Nos. 3,547,620 and 3,637,847 of J. F. Olin and German application No. 2,212,268 of Sumitomo Chemical Co. disclose the use of α-haloacetanilides as herbicides.

DESCRIPTION OF THE INVENTION

The N-carbamylalkyl 2,6-dialkyl-α-haloacetanilide compounds of the invention are represented by the formula (I):

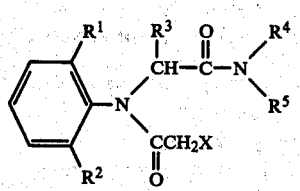

wherein $R^1$ and $R^2$ individually are lower alkyl groups of 1 to 6 carbon atoms; $R^3$ is hydrogen or lower alkyl of 1 to 6 carbon atoms; $R^4$ and $R^5$ individually are hydrogen, lower alkyl of 1 to 6 carbon atoms or lower alkenyl of 3 to 6 carbon atoms; and X is chlorine or bromine; with the proviso that $R^4$ and $R^5$ may together form a divalent alkylene group of 4 to 6 carbon atoms, or an ethyleneoxyethylene group ($-CH_2CH_2OCH_2CH_2-$).

Representative alkyl groups which $R^1$, $R^2$, $R^3$, $R^4$ and $R^5$ may represent include methyl, ethyl, propyl, isopropyl, butyl, sec-butyl, t-butyl, pentyl, isohexyl, hexyl, etc. Representative alkenyl groups which $R^4$ and $R^5$ may represent include allyl, 2-butenyl, 3-pentenyl, etc. Representative divalent alkylene groups formed by joining $R^4$ and $R^5$ include tetramethylene, pentamethylene and 3-methylpentamethylene.

Preferably $R^1$, $R^2$, $R^4$ and $R^5$ are alkyl of 1 to 3 carbon atoms, $R^3$ is hydrogen and X is chlorine.

The preferred compounds of formula (I) are those wherein $R^3$ is hydrogen and $R^4$ and $R^5$ are both alkyl.

The compounds of the invention may be prepared by alkylating a 2,6-dialkylaniline (II) with an α-haloamide (III) to produce an N-carbamylalkyl-2,6-dialkylaniline (IV) and subsequently acylating the N-carbamylalkyl-2,6-dialkylaniline (IV) with an α-haloacetyl halide (V) to give the N-carbamylalkyl-2,6-dialkyl-α-haloacetanilide product (I). This sequence of reactions is depicted by the following equations:

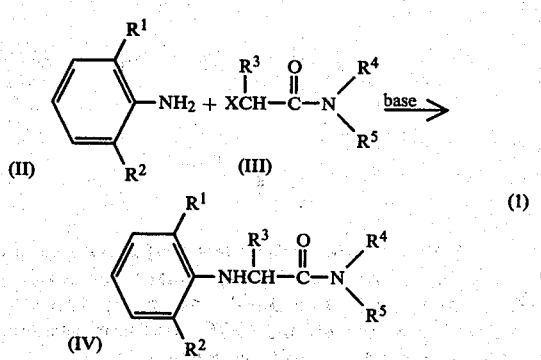

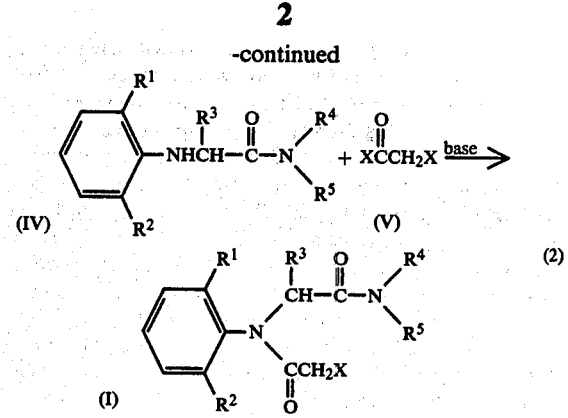

wherein $R^1$, $R^2$, $R^3$, $R^4$, $R^5$ and X have the same significance as previously defined.

The alkylation reaction (1) is conducted in the presence of a base. Suitable bases are inorganic alkali metal carbonates such as sodium carbonate or potassium carbonate. Generally, substantially equimolar amounts of reactants (II) and (III) and the base are employed. The reaction is conducted in inert polar organic solvents, e.g., apolar diprotic solvents such as dimethylformamide and acetonitrile, at reaction temperatures varying from 0° C. to 90° C., preferably from 20° C. to 50° C. The reaction pressure may be atmospheric, subatmospheric or superatmospheric. However, for convenience of conducting the reaction, the pressure is generally atmospheric. The reaction time will, of course, vary depending upon the reactants and the reaction temperature. Generally the reaction time is from 0.25 to 24 hours. The product (IV) is generally purified by conventional procedures, e.g., extraction, distillation or crystallization, before use in the acylation reaction (2).

The acylation reaction (2) is conducted by conventional procedures in the presence of an organic amine such as a trialkyl amine or pyridine. The reactants (IV) and (V) and the amine are generally contacted in substantially equimolar amounts in an inert organic solvent at a temperature of 0° to 50° C. Suitable inert organic solvents include ethyl acetate, methylene dichloride, dimethoxyethane, benzene, etc. The product is isolated and purified by conventional procedures such as extraction, distillation, chromatography, crystallization, etc.

The preparation of the compounds of the invention by the above reactions is illustrated by the following examples.

EXAMPLES

EXAMPLE 1—Preparation of N-(N',N'-diallylcarbamylmethyl)-2,6-diethyl-α-chloroacetanilide

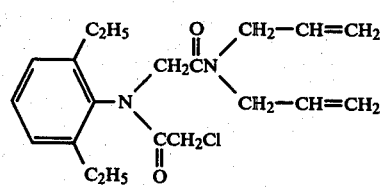

A 78-g (0.8 mol) sample of diallylamine was added dropwise to a stirred and cooled (dry-ice/acetone bath) solution of 80 g (0.4 mol) bromoacetylbromide in 200 ml methylene dichloride. The reaction mixture was allowed to warm to about 25° C. and stirred overnight.

The reaction mixture was then washed with water, aqueous sodium bicarbonate, again with water, dried over magnesium sulfate and evaporated under reduced pressure to give 38 g N,N-diallyl-α-bromoacetamide.

A mixture of 19 g (0.088 mol) N,N-diallyl-α-bromoacetamide (prepared above), 13.1 g (0.088 mol) 2,6-diethylaniline and 12.2 g (0.088 mol) potassium carbonate in 150 ml dimethylformamide was heated at 50°-65° C. for 24 hours. The reaction mixture was filtered and the filtrate was diluted with 300 ml water. The aqueous filtrate mixture was extracted with hexane. The hexane extracts were dried over magnesium sulfate and evaporated under reduced pressure to give a viscous oil. The oil was chromatographed on a silica-gel column. N-(N',N'-diallylcarbamylmethyl)-2,6-diethylaniline (12.3 g) was eluted from the column with 5% ether/hexane.

A solution of 2.48 g (0.0313 mol) pyridine in 25 ml ethyl acetate was added dropwise to a stirred and cooled (ice bath) solution of 8.93 g (0.0313 mol) N-(N',N'-diallylcarbamylmethyl)-2,6-diethylaniline (prepared above) and 3.54 g (0.0313 mol) chloroacetyl chloride in 150 ml of ethyl acetate. The reaction mixture was then stirred at about 25° C. overnight. The reaction mixture was diluted with 100 ml water. The aqueous layer was separated and extracted with diethyl ether. The ether extract and the organic layer were combined and washed with aqueous sodium bicarbonate and then water, dried over magnesium sulfate, and evaporated under reduced pressure to give a viscous oil. The oil was chromatographed on silica gel. Elution with 40% ether/hexane gave the product, N-(N',N'-diallylcarbamylmethyl)-2,6-diethyl-α-chloroacetaniline, as a yellow oil. Elemental analysis on the product ($C_{20}H_{27}ClN_2O_2$) showed: %Cl, calculated 9.77, found 10.2.

EXAMPLE 2

By a procedure similar to that of Example 1:

(a) α-chloroacetyl chloride and N-(N',N'-diallylcarbamylmethyl)-2,6-dimethylaniline were reacted to produce N-(N',N'-diallylcarbamylmethyl)-2,6-dimethyl-α-chloroacetanilide. Elemental analysis for $C_{18}H_{23}ClN_2O_2$ showed: %Cl, calculated 10.59, found 10.9.

(b) α-chloroacetyl chloride and N-(N',N'-dimethylcarbamylmethyl)-2,6-diethylaniline were reacted to produce N-(N',N'-dimethylcarbamylmethyl)-2,6-diethyl-α-chloroacetanilide as a white solid, m.p. 81°-82° C. Elemental analysis for $C_{16}H_{23}ClN_2O_2$ showed: %Cl, calculated 11.41, found 11.8.

(c) α-chloroacetyl chloride and N-(N',N'-dimethylcarbamylmethyl)-2,6-dimethylaniline were reacted to produce N-(N',N'-dimethylcarbamylmethyl)-2,6-dimethyl-α-chloroacetanilide, as a white solid, m.p. 85°-86.5° C. Elemental analysis for $C_{14}H_{19}ClN_2O_2$ showed: %Cl, calculated 12.54, found 12.1.

(d) α-chloroacetyl chloride and N-(N'-t-butylcarbamylmethyl)-2,6-dimethylaniline were reacted to produce N-(N'-t-butylcarbamylmethyl)-2,6-dimethyl-α-chloroacetanilide, as a white solid, m.p. 110°-112° C. Elemental analysis for $C_{16}H_{23}ClN_2O_2$ showed: %Cl, calculated 11.41, found 11.1.

(e) α-chloroacetyl chloride and N-(N'-t-butylcarbamylmethyl)-2,6-diethylaniline were reacted to produce N-(N'-t-butylcarbamylmethyl)-2,6-diethyl-α-chloroacetanilide, as a white solid, m.p. 118°-120° C. Elemental analysis for $C_{18}H_{27}ClN_2O_2$ showed: %Cl, calculated 10.46, found 10.2.

(f) α-chloroacetyl chloride and N-(N',N'-diethylcarbamylmethyl)-2,6-dimethylaniline were reacted to produce N-(N',N'-diethylcarbamylmethyl)-2,6-dimethyl-α-chloroacetanilide, as a yellow oil. Elemental analysis for $C_{16}H_{23}ClN_2O_2$ showed: %Cl, calculated 11.41, found 11.9.

(g) α-chloroacetyl chloride and N-(N',N'-diethylcarbamylmethyl)-2,6-diethylaniline were reacted to produce N-(N',N'-diethylcarbamylmethyl)-2,6-diethyl-α-chloroacetanilide, a yellow oil. Elemental analysis for $C_{18}H_{27}ClN_2O_2$ showed: %Cl, calculated 10.46, found 10.4.

(h) α-chloroacetyl chloride and N-(N'-sec-butylcarbamylmethyl)-2,6-diethylaniline were reacted to produce N-(N'-sec-butylcarbamylmethyl)-2,6-diethyl-α-chloroacetanilide as a white solid, m.p. 120°-122° C. Elemental analysis for $C_{18}H_{27}ClN_2O_2$ showed: %Cl, calculated 10.46, found 10.3.

(i) α-chlororacetyl chloride and N-(N'-sec-butylcarbamylmethyl)-2,6-dimethylaniline were reacted to produce N-(N'-sec-butylcarbamylmethyl)-2,6-dimethyl-α-chloroacetanilide as a white solid, m.p. 97°-99° C. Elemental analysis for $C_{18}H_{23}ClN_2O_2$ showed: %Cl, calculated 10.41, found 10.40.

(j) α-chloroacetyl chloride and N-(carbamylmethyl)-2,6-dimethylaniline were reacted to produce N-(carbamylmethyl)-2,6-dimethyl-α-chloroacetanilide, as a white solid, m.p. 139°-141° C. Elemental analysis for $C_{12}H_{15}ClN_2O_2$ showed: %Cl, calculated 13.92, found 13.70.

(k) α-chloroacetyl chloride and N-(carbamylmethyl)-2,6-diethylaniline were reacted to produce N-(carbamylmethyl)-2,6-diethyl-α-chloroacetanilide, m.p. 150°-152° C. Elemental analysis for $C_{14}H_{19}ClN_2O_2$ showed: %Cl, calculated 12.54, found 12.6. The structural formula of this product is

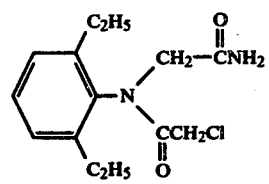

(m) α-chloroacetyl chloride and N-(piperidinocarbonylmethyl)-2,6-dimethylaniline were reacted to produce N-(piperidinocarbonylmethyl)-2,6-dimethyl-α-chloroacetanilide, m.p. 109°-111° C. Elemental analysis for $C_{16}H_{21}ClN_2O_2$ showed: %Cl, calculated 11.48, found 11.5. The structural formula of this product is

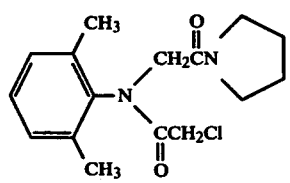

If N-(morpholinocarbonylmethyl)-2,6-dimethylaniline were employed in this experiment in place of the N-(piperidinocarbonylmethyl)-2,6-dimethylaniline reactant, the product would be N-(morpholinocarbonylmethyl)-2,6-dimethyl-α-chloroacetanilide.

(n) α-chloroacetyl chloride and N-(piperidinocarbonylmethyl)-2,6-diethylaniline were reacted to produce N-(piperidinocarbonylmethyl)-2,6-diethyl-α-chloroacetanilide, m.p. 123°–124° C. Elemental analysis for $C_{18}H_{25}ClN_2O_2$ showed: %Cl, calculated 10.52, found, 10.2.

(o) α-chloroacetyl chloride and N-[1-(N,N-dimethylcarbamyl)ethyl]-2,6-dimethylaniline were reacted to produce N-[1-(N,N-dimethycarbamyl)ethyl]-2,6-dimethyl-α-chloroacetanilide, m.p. 112°–114° C. Elemental analysis for $C_{15}H_{21}ClN_2O_2$ showed: %Cl, calculated 11.95, found 11.7. The structural formula for this product is

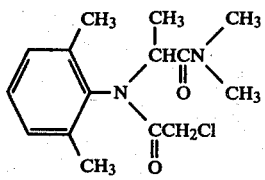

(p) α-chloroacetyl chloride and N-[1-(N′,N′-dimethylcarbamyl)ethyl]-2,6-diethylaniline were reacted to produce N-[1-N′,N′-dimethylcarbamyl)ethyl]-2,6-dimethyl-α-chloroacetanilide, m.p. 100°–102° C. Elemental analysis for $C_{17}H_{25}ClN_2O_2$ showed: %Cl, calculated 10.9, found 10.7.

UTILITY

The α-haloacetanilide compounds of the present invention are, in general, herbicidal in both pre- and post-emergent applications. For pre-emergent control of undesirable vegetation, the compounds will be applied in herbicidal quantities to the environment or growth medium of the vegetation, e.g., soil infested with seeds and/or seedlings of such vegetation. Such application will inhibit the growth of or kill the seeds, germinating seeds and seedlings. For post-emergent applications, the compounds of the present invention will be applied directly to the foliage and other plant parts. Generally they are effective against weed grasses as well as broad-leaved weeds. The compounds are particularly effective as pre-emergent herbicides against grasses.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 2 to 60 kg/ha, and the preferred rate is in the range of 5 to 40 kg/ha.

Pre-emergent herbicidal tests on representative compounds of this invention were made using the following method:

An acetone solution of the test α-haloacetanilide was prepared by mixing 750 mg α-haloacetanilide, 220 mg of a nonionic surfactant and 25 ml of acetone. This solution was added to approximately 125 ml of water containing 156 mg of surfactant.

Seeds of the test vegetation were planted in a pot of soil and the solution was sprayed uniformly onto the soil surface at a dose of 33 mcg per $cm^2$. The pot was watered and placed in a greenhouse. The pot was watered intermittently and was observed for seedling emergence, health of emerging seedlings, etc., for a 3-week period. At the end of this period the herbicidal effectiveness of the solution was rated based on the physiological observations. A 0-to-100 scale was used, 0 representing no phytotoxicity, 100 representing complete kill. The results are tabulated in Table I.

TABLE I

| Compound No. | Herbicidal Effectiveness | | | | | |
|---|---|---|---|---|---|---|
| | O | W | C | M | P | L |
| 1 | 0 | 80 | 0 | 0 | 0 | 0 |
| 2a | 25 | 98 | 90 | 15 | 20 | 0 |
| 2b | 80 | 100 | 100 | 100 | 100 | 90 |
| 2c | 100 | 100 | 100 | 100 | 100 | 100 |
| 2d | 93 | 100 | 100 | 0 | 65 | 45 |
| 2e | 15 | 98 | 90 | 0 | 20 | 0 |
| 2f | 100 | 100 | 100 | 100 | 100 | 100 |
| 2g | 75 | 98 | 100 | 0 | 75 | 25 |
| 2h | 88 | 100 | 100 | 0 | 0 | 0 |
| 2i | 70 | 100 | 100 | 50 | 25 | 60 |
| 2j | 60 | 100 | 100 | 0 | 10 | 50 |
| 2k | 55 | 100 | 100 | 0 | 35 | 78 |
| 2m | 100 | 100 | 100 | 30 | 80 | 40 |
| 2n | 93 | 100 | 100 | 0 | 0 | 0 |
| 2o | 0 | 20 | 0 | 40 | 35 | 0 |
| 2p | 0 | 20 | 0 | 0 | 0 | 0 |

O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

What is claimed is:
1. A compound of the formula

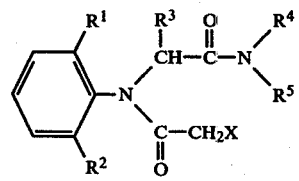

wherein $R^1$ and $R^2$ individually are alkyl of 1 to 6 carbon atoms; $R^3$ is hydrogen; $R^4$ and $R^5$ individually are hydrogen, alkyl of 1 to 6 carbon atoms or alkenyl of 3 to 6 carbon atoms; and X is chlorine or bromine, with the proviso that R⁴ and R⁵ may together form a divalent alkylene group of 4 to 6 carbon atoms or —CH₂CH₂OCH₂CH₂—.

2. The compound of claim 1 wherein and X is chlorine.

3. The compound of claim 2 wherein R⁴ and R⁵ are alkyl.

4. The compound of claim 3 wherein R¹, R², R⁴ and R⁵ are alkyl of 1 to 3 carbon atoms.

5. The compound of claim 4 wherein R¹, R², R⁴ and R⁵ are methyl.

6. The compound of claim 4 wherein R¹ and R² are methyl, and R⁴ and R⁵ are ethyl.

7. The compound of claim 2 wherein R⁴ and R⁵ are alkenyl.

8. The compound of claim 2 wherein R⁴ is hydrogen and R⁵ is alkyl of 1 to 3 carbon atoms.

9. The compound of claim 2 wherein R⁴ is hydrogen and R⁵ is alkenyl.

10. The compound of claim 2 wherein R⁴ and R⁵ are hydrogen.

11. The compound of claim 2 wherein R⁴ and R⁵ together form a divalent alkylene group or —CH₂CH₂OCH₂CH₂—.

12. The compound of claim 11 wherein R⁴ and R⁵ together form tetramethylene and R¹ and R² are methyl.

13. N-(N',N'-diallylcarbamylmethyl)-2,6-dimethyl-α-chloroacetanilide, according to claim 7.

14. A compound of the formula

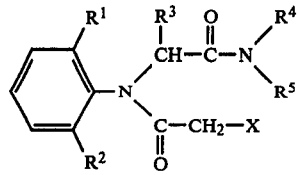

wherein R¹ and R² individually are methyl or ethyl, R³ is hydrogen, R⁴ and R⁵ individually are methyl or ethyl, and X is chlorine.

15. The compound of claim 14 wherein R¹ and R² individually are methyl or ethyl, R⁴ is hydrogen, methyl or ethyl, and R⁵ is methyl or ethyl.

16. N-(N',N'-dimethylcarbamylmethyl)2,6-dimethyl-alpha-chloroacetanilide, according to claim 14.

17. A plant-growth-inhibiting composition which comprises an effective amount of the compound of claim 14 admixed with a biologically inert carrier.

18. A method for inhibiting the growth of vegetation which comprises applying thereto an effective amount of the compound of claim 14.

19. The method of claim 18 wherein the compound is N-(N',N'-dimethylcarbamylmethyl)-2,6-dimethyl-alpha-chloroacetanilide.

* * * * *